(12) United States Patent
Ripart

(10) Patent No.: US 6,385,485 B1
(45) Date of Patent: May 7, 2002

(54) CONTINUOUSLY MONITORING CARDIAC EVENTS IN AN ACTIVE IMPLANTABLE MEDICAL DEVICE

(75) Inventor: Alain Ripart, Gif-sur-Yvette (FR)

(73) Assignee: Ela Medical S.A., Montrouge (FR)

( * ) Notice: Subject to any disclaimer, the term of this patent is extended or adjusted under 35 U.S.C. 154(b) by 0 days.

(21) Appl. No.: 09/467,999

(22) Filed: Dec. 20, 1999

(51) Int. Cl.$^7$ .............................. A61B 5/0432

(52) U.S. Cl. ...................... 600/513; 600/523

(58) Field of Search .................. 600/509, 513, 600/515, 518, 522, 523; 607/18, 19

(56) References Cited

U.S. PATENT DOCUMENTS

| | | | | |
|---|---|---|---|---|
| 3,706,308 A | * | 12/1972 | John et al. ............. | 128/2.06 |
| 3,721,230 A | * | 3/1973 | Ziernicki .............. | 128/2.1 |
| 4,407,288 A | * | 10/1983 | Langer et al. .......... | 128/419 |
| 5,312,446 A | * | 5/1994 | Holschbach et al. ...... | 607/9 |

OTHER PUBLICATIONS

PCT WO/89/01803, Mar. 9, 1989 (21) International Application No.: PCT/SE88/00446; (22) International Filing Date Aug. 31, 1988.*

* cited by examiner

Primary Examiner—Kennedy Schaetzle
(74) Attorney, Agent, or Firm—Orrick Herrington & Sutcliffe, LLP

(57) ABSTRACT

An active implantable medical device, in particular a pacemaker, defibrillator and/or cardiovertor, including a circuit for recording cardiac events. This device records cardiac events or parameters representative of cardiac events, such that the recording of the current cardiac events replaces that of the oldest events previously recorded. The device inhibits the recording operation so as to stop the recording of the cardiac events and/or event markers in response to it being established that the patient has died. The inhibition can be obtained by detecting spontaneous or stimulated cardiac activity, advantageously combined with the detection of a parameter indicative of the patient's metabolic demand, such as the activity or effort of the patient, so that the inhibition occurs only in the event of the detection of an absence of cardiac activity confirmed by an absence of activity and/or effort of the patient.

7 Claims, 1 Drawing Sheet

CONTINUOUSLY MONITORING CARDIAC EVENTS IN AN ACTIVE IMPLANTABLE MEDICAL DEVICE

FIELD OF THE INVENTION

The present invention relates to "active implantable medical devices" as defined by the Jun. 20, 1990 directive No. 90/385/CEE of the Council of the European Communities, and more specifically to pacemaker, defibrillator and/or cardiovertors devices equipped with a data recording and storage function known as a "Holter" function.

BACKGROUND OF THE INVENTION

The Holter function provides for a continuous monitoring of the patient's cardiac rhythm parameters, as well as storing the so-called "event markers" (for such events as stimulation, detection outside a refractory period, capture, etc.), to evaluate the stability of the parameter(s) for diagnostic and/or therapeutic purposes. An advantage of the Holter function is, in the event of the death of a patient, an analysis of the data collected (i.e., recorded and stored in memory) during the time preceding the death can be used to help determined the cause of death. It is thus possible to determine if the death was or was not cardiac in origin, and, in the case of a death of cardiac origin, the cause, particularly in the case of a defibrillator or cardiovertor. For example, it is important to know if the cardioversion or defibrillation pulses were or were not delivered by the implant, under which circumstances, for how long, what was the response to the pulse(s), etc.

In this respect, reference is made to the article of Grubman et al., entitled "Cardiac Death and Stored Electrograms in Patients With Third Generation Implantable Cardioverter-Defibrillators", *JACC.,* Vol. 32, No. 4, October 1998, pp. 1056–62, which gives an account of a statistical analysis carried out postmortem in this manner on tens of patients. However, in a certain number of cases the recording data is no longer available, mainly owing to the fact that, to keep the data, it is essential to stop quickly the implant from recording new data after the death. This is because otherwise, the device continues its recording, and, therefore, would replace gradually the relevant data with a flat electrocardiogram, corresponding to the cardiac rhythm data acquired during the period following death. Indeed, being an implanted device, the information storage capacity is limited, typically to a duration of from twenty to thirty minutes, and the recording is made in a first-in, first-out loop, i.e., as long as the recording continues, the most recent data replaces the oldest data.

The above-mentioned article also deplores the absence of data recorded (e.g., an intracardiac ECG recording) in a great number of cases, which leads to an assumption that the death was not the immediate result of a tachyarrhythmia, but without this assumption being able to be corroborated by an analysis of the heartbeat rate before the moment of the death. In the particular cases of the study reported by this article, the authors note that the heartbeat rate data before death was absent in 69% of the cases, and thus the study of the causes of death which need to be carried out are only for the remaining 31% of the population considered.

In addition, the publication WO-A-89/01803 describes a pacemaker, which records the cardiac activity and stops the recording of the data after a certain time if hemodynamic sensors indicate the stop of cardiac circulation. However, the use of sensors of the blood flow is not easy to implement in association with a pacemaker.

OBJECTS AND SUMMARY OF THE INVENTION

It is an object of the invention to overcome the above-mentioned limitations, by providing an active implantable medical device that detects and automatically indicates a situation establishing the death of the patient, and freezes the last acquired recordings of the cardiac information, namely the heartbeat rate data and/or event markers, for the purpose of later analysis.

To this end, the invention is directed to an active implanted medical device, particularly, a pacemaker, defibrillator and/or cardiovertor, including a circuit means for recording cardiac events and/or parameters representative of these events, (commonly known as "event markers" discussed above), and in which the current recorded information of cardiac events replaces that of the oldest acquired information, and a circuit means for inhibiting the recording means, which inhibiting circuit means is able to stop the recording of the cardiac events and/or event markers in the event of an established death of the patient. The data may be continuously recorded, or intermittently recorded, or recorded in some other manner. This device is preferably characterized in that the inhibiting circuit means detects a spontaneous and/or electrostimulated cardiac activity, and a parameter indicative of a patient's metabolic demand, these two types of detection being advantageously combined so as to operate the inhibiting circuit means to stop the recording only in the event of the detection of an absence of cardiac activity parameter, confirmed by an absence of a parameter indicative of a patient's metabolic demand. The patient's metabolic demand parameter is preferably one or both of a patient physical activity parameter and a patient physiological parameter corresponding to patient effort.

BRIEF DESCRIPTION OF THE DRAWINGS

Further characteristics, features, and advantages of the present invention will be apparent upon consideration of the following detailed description of the present invention, taken in conjunction with the drawing shown in FIG. 1, which is a block diagram showing a device according to an embodiment of the invention.

DETAILED DESCRIPTION OF THE INVENTION

Figure 1:
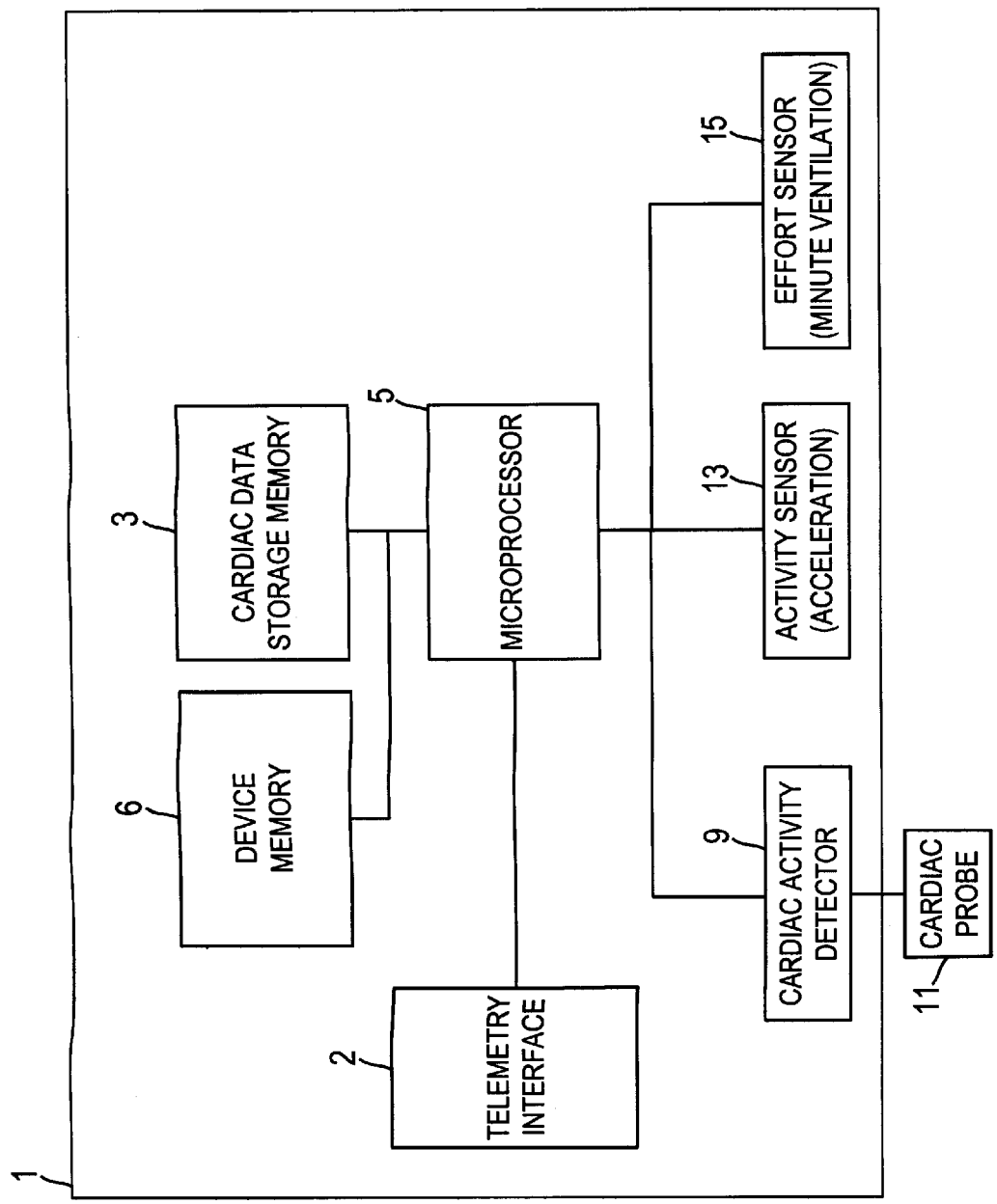

One now will describe, in conjunction with FIG. 1, as an exemplary implementation, a preferred embodiment of the present invention.

Advantageously, the present invention can be incorporated in an existing implant such as a pacemaker, a defibrillator and/or a cardiovertor controlled by software, the particular functions of the invention being put in effect by suitable programming or reprogramming of this software (e.g., downloading by telemetry to the implanted device memory 6 a software routine for performing the stated functions).

These devices 1, in a known manner, are equipped with circuit means 9 making it possible to detect a cardiac activity, which activity is able to have a double origin, that is to say a spontaneous activity, which is then sensed as such by the device, and a stimulated activity, which one can then detect, for example, by the circuit means disclosed in WO-A-93/02741. This circuit describes means making it possible to know if, in the event of stimulation, this stimulation was effective, by the detection of a post-stimulation "capture" signal emitted by the myocardium.

The absence of spontaneous or stimulated cardiac activity, thus detected, is a first condition, according to the invention, to stop the recording in memory 3 of the information, namely the heartbeat rate, or the parameters representative of the heartbeat rate, by the Holter function of the device.

If only this criterion is used, the system can, however, be misled in certain situations. For example, in the case of a dislodgment of the cardiac probe 1, although the heart continues to beat, the displaced probe 11 will not sense either a spontaneous depolarization or an event signal following a stimulation. To minimize this risk, in accordance with an embodiment of the present invention, one can advantageously combine the above-mentioned criterion of an absence of cardiac activity with a second criterion of an absence of a parameter indicating the metabolic needs of the patient, e.g., activity and/or effort of the patient, and then stop the recording of the heartbeat rate, only when these two criteria are cumulatively fulfilled.

The second criterion can in particular be put into effect by means of an activity sensor 13 and/or an effort sensor 15, preferably the former. These sensors are well known in the art and used for the control of various functions of the pacemaker 1. The term "activity sensor" refers to sensor to detect quickly a change of the physical activity of the patient bearing the apparatus, typically an accelerometer or the "sensor G" device, as described, for example, in EP-A-0 550 293 and its corresponding U.S. Pat. No. 5,330,510 (ELA Medical) or EP-A-0 750 920 and its corresponding U.S. Pat. No. 5,722,996 (ELA Medical). The term "effort sensor" refers to a sensor of a physiological parameter that is able to given an adequate representation of the metabolic needs of the patient at a given moment, typically a minute ventilation sensor or a "device sensor MV", according to the known and traditional techniques, for example, as disclosed in EP-A-0 151 689 or EP-A-0 750 920 and its U.S. Pat. No. 5,722,996 (ELA Medical). The latter documents also describe a pacing system that uses a dual sensor, one physiological effort sensor, and one activity sensor.

The device thus combines the disappearance of the cardiac activity (cardiac activity detector 9) with a detection of patient activity (sensor 13) and/or effort (sensor 15), so as to avoid an interruption of recording of the heartbeat rate, for example, caused by a simple dislodgment of the probe 11. In this case, the sensor 13, 15 (or sensors if more than one sensor is used) will reveal the presence of patient activity and/or effort, and will thus indicate that the absence of detection of the heartbeat rate is due to a cause other than the death of the patient.

On the other hand, the disappearance of the cardiac activity combined with the absence of signals sensed by a sensor MV 15 or a sensor G 13 is indicative of the establishment of the death of the patient. In this case, the device will freeze the information contained in its Holter memories 3, so that it will then be possible to transmit, e.g., by means of a radio frequency telemetry connection 2, the information stored in these memories 3 to an external system, such as a programmer, for an analysis. For example, an absence of any detection of the signal by sensor MV 15 for a predetermined time period, such as at least twenty seconds, means that the pacemaker sensor is "OFF" and no signal is detected. The same principle applies for the activity sensor G 13, although a shorter time period can be used (e.g., ten seconds). In the presence of two sensors 13, 15, a confirmation over time in that both signals are absent can thus be put into effect for greater reliability in operating the inhibiting circuit to stop the recording.

According to an embodiment of the invention, during operation of an implant device 1 data from the cardiac sensor 9 is provided to the microprocessor 5. This data is stored in a cardiac data storage memory 3. The microprocessor 5 also monitors signals from the activity sensor 13 and effort sensor 15. In the event the microprocessor 5 detects no spontaneous or stimulated cardiac activity from the cardiac activity detector 9 and concurrently detects no activity signal and/or no effort signal from the activity sensor 13 and the effort sensor 15, respectively, the microprocessor 5 inhibits storage of additional data in the memory 3. Data from the memory 3 can then be retrieved post-mortem, via the telemetry interface 2.

One skilled in the art will appreciate that the present invention can be practiced by other than the preferred embodiments, which are presented for purposes of illustration and not of limitation.

I claim:

1. An active implantable medical device having means for recording information representative of cardiac events of a patient, and in which the recording means operates to replace the oldest recorded information with the newest recorded information, further comprising means for inhibiting the recording means from recording additional information in response to an established death of the patient, wherein the inhibiting means comprises means for detecting a cardiac activity and means for detecting a parameter indicative of patient metabolic demand.

2. The device of claim 1 wherein said recorded information further comprises at least one of a spontaneous cardiac event, a stimulated cardiac event, and an event marker representative of a cardiac event.

3. The device of claim 1 wherein said parameter indicative of patient metabolic demand further comprises one of a patient activity parameter and a patient effort parameter.

4. The device of claim 3, wherein the means for detecting a patient metabolic demand parameter further comprises an acceleration sensor.

5. The device of claim 3, wherein the means for detecting a patient metabolic demand parameter further comprises a minute ventilation sensor.

6. The device of claim 1, wherein the inhibiting means operates to inhibit recording information only in response to a detection of an absence of cardiac activity and an absence of said patient metabolic demand parameter.

7. The device of claim 1, wherein the inhibiting means operates to inhibit recording information only in response to a detection of an absence of cardiac activity and an absence of said patient metabolic demand parameter for a predetermined period of time.

* * * * *